United States Patent [19]

Holtkamp

[11] Plant 4,414

[45] May 15, 1979

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Isselburg, Fed. Rep. of Germany

[21] Appl. No.: 880,051

[22] Filed: Feb. 22, 1978

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An african violet named Ohio having strong and upright flower stems which support 7–12 red-purple flowers on each stem, with the flowers having 5–15 petals. The flowers have a semi-double appearance when several petals appear above the main petals. The plant is compact and fast growing, and has dark green, velvety leaves.

1 Drawing Figure

The present invention comprises a new and distinct cultivar of african violet plant, botanically known as *Saintpaula ionantha,* and referred to by the cultivar name Ohio. Ohio was identified during the breeding and selection process by the designation B 265/5 - 65/77 and is a product of a planned breeding program. Ohio is principally characterized by its single to semi-double red-purple flowers, strong erect flower stems with up to 12 flowers per stem, the number of petals on each flower varying from 5–15, and are non-dropping.

The new cultivar was originated from a cross made in a controlled breeding program in Isselburg, Rhineland, Germany. The female, or seed parent was XIX 2 white-red, an unpatented cultivar. The male, or pollen parent is also unpatented, and identified as FI pink frilled (color 62 A).

Ohio was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Ohio, which in combination distinguish this african violet as a new and distinct cultivar:

(1) Strong, straight and upright flower stems.

(2) 7–12 red-purple flowers on each flower stem, with some flowers being single and others having up to 10 additional petals above the main petals, thereby giving the flowers a semi-double appearance. The flowers are non-dropping.

(3 ) A plant in full bloom has 7–9 flower stems.

(4) Very compact and fast growing habit.

(5) Dark green, velvety leaves.

The accompanying photographic drawing shows a typical specimen plant of the new cultivar. The colors appearing in the photograph are as true as possible with color illustrations of this type.

In the following description, flower color values are referenced to Horticultural Color Chart (Wilson), and the color values of foliage, buds, sepas, male parent, and reproductive organs are referenced to RHS Color Chart, 1966 edition. It is noted that it was difficult to obtain exact color values for the flowers, and the color values indicated below are as accurate as possible.

Botanical classification: *Saintpaulia ionantha,* Ramat. cv Ohio

Parentage:

*Male Parent.*—F I pink frilled (color 62 A)

*Female Parent.*—XIX 2 white-red.

Propagation: The new cultivar holds its distinguishing characteristics through successive propagations by leaf cuttings and by division of shoots.

Plant: From 8 cm. to 9 cm. tall when grown in pots, and approximately 25 cm. in diameter when fully grown.

*Leaves.*—General Form: Oblong. Diameter: Up to 60 mm. Texture: Tender, velvety. Aspect: Dark green, border of leaves serrated. Veins: Well pronounced, reddish. Color (upperside): 131 A, with the leaves being somewhat darker than shown in the photograph. Color (underside): 71 A, red-purple. Petiole: red-brown.

Flowers:

*Buds.*—Round shape, diameter 7–8 mm., color 70 B.

*Sepals.*—Five, 5–6 mm. long, spear-shaped. Color: 59 A. Calyx: flat funnel. Aspect: receptacle and seed vessel joined. Peduncle: 25–30 mm. long, straight.

Individual flowers:

*Size.*—35–40 mm. in total flower diameter.

*Color.*—Upperside: 732 to 732/1 being somewhat darker than shown in the photograph. Underside: lighter than 732.

*Borne.*—The flower stems carry up to 12 single or semi-double flowers on peduncles 25–30 mm. long.

*Shape and size of petals.*—When there are only 5 petals on the flower, 2 of them are small, and 3 are large. The three large petals are 23 mm. long and 19–20 mm. wide; the two small petals are 17 mm. long and 16 mm. wide. The flowers frequently have on top of the main petals up to 10 additional petals which causes the flower to appear to have double blossoms. Strong straight flower stem, up to 12 flowers on one flower stem.

*Flowering time.*—8–10 weeks after potting the first flowers appear; 9–12 weeks after potting, the flower is fully in bloom.

Reproductive organs:

*Stamens.*—At least two stamens.

*Anthers.*—4 or more anthers.

*Arrangement.*—The stamens sit on short stems around the seed vessel and are fused with the receptacle. They are partially covered by petals.

*Filaments.*—Reddish in color, 5 mm. long; some petals joined to it.

*Styles.*—6–7 mm. long, color 70 A; sometimes joined to petals.

*Pollen color.*—7 C.

Roots: Well developed roots; the tips are white, older roots have a brownish color.

Disease resistance: Good disease resistance to date.

General observation: Ohio is a vigorous and fast grower, with up to 12 flowers sitting on strong erect flower stems. Each flower has a varying number of petals from 5–15, with petals in excess of five appearing above the main petals thereby giving the flower a semi-double appearance. The flowers are red-purple and non-dropping, and provide a pleasant contrast with the dark green leaves.

I claim:

1. A new and distinct cultivar of african violet known by the cultivar name Ohio and characterized by the combined features of strong and upright flower stems which support 7–12 red-purple flowers on each stem, with the flower having 5–15 petals, with the flower having a semi-double appearance when several petals appear above the main petals; very compact and fast growing habit, and dark green, velvety leaves.

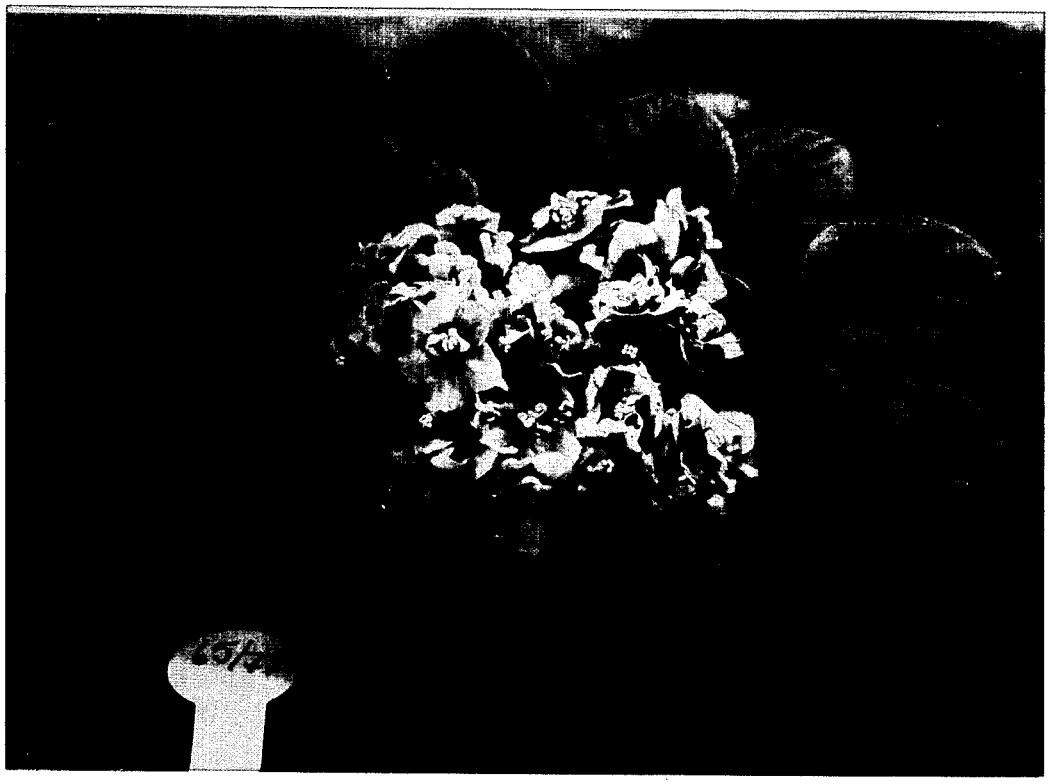

* * * * *